United States Patent
Sinha et al.

(10) Patent No.: US 9,091,622 B2
(45) Date of Patent: Jul. 28, 2015

(54) CAPILLARY-BASED CALIBRATION STANDARDS FOR MEASUREMENT OF PERMEABILITY

(71) Applicants: Somnath Sinha, Houston, TX (US); Edward M. Braun, Sugar Land, TX (US); Quinn R. Passey, Kingwood, TX (US); Sergio A. Leonardi, Pearland, TX (US); Alexander C. Wood, III, Meadows Place, TX (US); Timothy E. Zirkle, Houston, TX (US); Ryan A. Kudva, Manvel, TX (US)

(72) Inventors: Somnath Sinha, Houston, TX (US); Edward M. Braun, Sugar Land, TX (US); Quinn R. Passey, Kingwood, TX (US); Sergio A. Leonardi, Pearland, TX (US); Alexander C. Wood, III, Meadows Place, TX (US); Timothy E. Zirkle, Houston, TX (US); Ryan A. Kudva, Manvel, TX (US)

(73) Assignee: ExxonMobil Upstream Research Company, Houston, TX (US)

(*) Notice: Subject to any disclaimer, the term of this patent is extended or adjusted under 35 U.S.C. 154(b) by 432 days.

(21) Appl. No.: 13/660,922

(22) Filed: Oct. 25, 2012

(65) Prior Publication Data

US 2013/0152671 A1 Jun. 20, 2013

Related U.S. Application Data

(60) Provisional application No. 61/578,020, filed on Dec. 20, 2011.

(51) Int. Cl.
*G01N 15/08* (2006.01)
*G01N 1/28* (2006.01)

(52) U.S. Cl.
CPC .... *G01N 15/0826* (2013.01); *G01N 2001/2893* (2013.01)

(58) Field of Classification Search
CPC .................................................. G01M 3/007
USPC ............................................................ 73/1.17
See application file for complete search history.

(56) References Cited

U.S. PATENT DOCUMENTS

| | | | | | |
|---|---|---|---|---|---|
| 2,499,977 | A | * | 3/1950 | Scott | 148/527 |
| 3,751,271 | A | * | 8/1973 | Kimura et al. | 501/85 |
| 4,561,289 | A | * | 12/1985 | Jones | 73/38 |
| 5,226,310 | A | * | 7/1993 | Steiger | 73/38 |
| 5,564,067 | A | * | 10/1996 | Hendricks | 428/566 |
| 7,255,166 | B1 | | 8/2007 | Weiss | |

(Continued)

FOREIGN PATENT DOCUMENTS

| EP | 1898876 | 12/2008 |
|---|---|---|
| WO | WO2006/132861 | 12/2006 |

OTHER PUBLICATIONS

American Petroleum Institute, (1998) "Recommended Practices for Core Analysis. Recommended Practice 40", Second Edition, API Publishing Services, Washington, D.C., p. 6-2.

(Continued)

*Primary Examiner* — Hezron E Williams
*Assistant Examiner* — Mark A Shabman
(74) *Attorney, Agent, or Firm* — ExxonMobil Upstream Research-Law Department

(57) ABSTRACT

A calibration standard or check plug provides calibration standards in the permeability range of 10-10,000 nanoDarcy. The check plug is of similar exterior dimensions to a core sample that would be used with existing permeameters. The check plug is constructed from an impermeable material that is insensitive to moisture. The check plug has one or more channels of known diameter from which the permeability may be calculated. Methods for use thereof and methods of manufacture thereof are also disclosed.

22 Claims, 3 Drawing Sheets

(56) References Cited

U.S. PATENT DOCUMENTS

| | | | |
|---|---|---|---|
| 7,585,817 | B2 | 9/2009 | Pope et al. |
| 7,833,946 | B2 | 11/2010 | Bailey |
| 2002/0189325 | A1* | 12/2002 | Bowen et al. ............ 73/38 |
| 2006/0143895 | A1* | 7/2006 | Liu et al. ............ 29/527.1 |
| 2008/0154563 | A1 | 6/2008 | Kumar et al. |
| 2011/0108271 | A1 | 5/2011 | Hinkel et al. |
| 2012/0152548 | A1 | 6/2012 | Hinkel et al. |

OTHER PUBLICATIONS

American Petroleum Institute, (1998) "Recommended Practices for Core Analysis. Recommended Practice 40", Second Edition, API Publishing Services, Washington, D.C., p. 2-11.

American Petroleum Institute, (1998) "Recommended Practices for Core Analysis. Recommended Practice 40", Second Edition, API Publishing Services, Washington, D.C., Section 6.

ATEQ, F5200 Leak Tester, (2010) http://www.ateq-leaktesting.com/products-services/product/f5200_leak_tester?page=4 website accessed Jul. 27, 2010.

Bird, R.B., et al. (2002) "Flow Through a Circular Tube", *Transport Phenomena*, Second Edition, John Wiley & Sons, Inc., New York, p. 51.

Bird, R.B., et al. (2002) "Flow Through a Circular Tube", *Transport Phenomena*, Second Edition, John Wiley & Sons, Inc., New York, p. 52.

Cincinnati Test Systems, (2011) Crimped Capillary Model (CP,CPH): http://www.cincinnati-test.com/crimped-capillary-model-p-10002-1-en-l-en.html website accessed Jul. 27, 2011.

Coretest Systems, Inc., (2011),CKP Series Permeability-Porosity Checkplugs, website: http://www.coretest.com/product_detail.php?p_id=27 accessed Jul. 27, 2011.

Furness Controls (2011), Low Pressure Laminar Flow Elements, FC0096, website http://www.furnesscontrols.com/pdf/FCO96.pdf, accessed Jul. 27, 2011.

National Physical Laboratory, (2011) Mean velocity, free path and size of molecules, Chart 2.2.4, showing chart from Hirschfelder, Curtiss and Bird, "Molecular Theory of Gases and Liquids", Wiley, New York (1954), website www.kayelaby.npl.co.uk/general_physics/2_2/2_2_4.html, accessed Jul. 2011.

Luffel, D. L. et al. (1992) "New Core Analysis Methods for Measuring Reservoir Rock Properties of Devonian Shale," *Journal of Petroleum Technology*, Nov. 1992, pp. 1184-1190.

Luffel, D.L. et al., (1993) "Matrix Permeability Measurement of Gas Productive Shales," *SPE 26633*, presented at the Society of Petroleum Engineers Technical Conference, Houston (1993).

Passey, Q. R., et al., (2010) "From Oil-Prone Source Rock to Gas-Producing Shale Reservoir—geologic and Petrophysical Characterization of Unconventional Shale-Gas Reservoirs." *SPE 131350*, presented at the CPS/SPE International Oil & Gas Conference and Exhibition in China, held in Beijing, China.

Spears, R. W., et al., (2011) "Shale Gas Core Analysis: Strategies for Normalizing Between Laboratories and a Clear Need for Standard Materials", *SPWLA 52nd Annual Logging Symposium* held in Colorado Springs, Colorado, May 14-18, 2011; Paper A.

Vinci Technologies (2011) Calibrated permeability check plugs website: http://www.vinci-technologies.com/products-explo.aspx?IDM=753561&IDR=82292&IDR2=82525 , accessed Jul. 26, 2011.

* cited by examiner

US 9,091,622 B2

CAPILLARY-BASED CALIBRATION STANDARDS FOR MEASUREMENT OF PERMEABILITY

CROSS-REFERENCE TO RELATED APPLICATION

This application claims the priority benefit of U.S. Provisional Patent Application 61/578,020 filed Dec. 20, 2011 entitled CAPILLARY-BASED CALIBRATION STANDARDS FOR MEASUREMENT OF PERMEABILITY, the entirety of which is incorporated by reference herein.

FIELD OF THE INVENTION

Embodiments of the present invention are directed toward the measurement of permeability of a core sample, and more specifically, towards the calibration of the equipment that measures the permeability of a core sample.

BACKGROUND

This section is intended to introduce various aspects of the art, which may be associated with exemplary embodiments of the present techniques. This discussion is believed to assist in providing a framework to facilitate a better understanding of particular aspects of the present techniques. Accordingly, it should be understood that this section should be read in this light, and not necessarily as admissions of prior art.

When hydrocarbons, such as oil and/or natural gas, are produced from underground reservoirs, they must first flow through pores in rock before reaching a wellbore. The ease with which hydrocarbons flow through the rock is known as the permeability of the rock, and is a key factor in the economic success of petroleum production.

It is common in the oil and gas industry to measure permeability on rock samples, such as core samples taken from oil and gas reservoirs. This is one of several laboratory tests providing data for use by engineers in understanding flow in a petroleum reservoir and determining the economics of a petroleum production operation. Other tests include porosity, oil saturation, water saturation, mineral content, and physical properties of oil.

The fundamental unit of permeability is the Darcy (in SI units, 1 Darcy=$9.869233 \times 10^{-13}$ m$^2$). However, rock in most oil and gas reservoirs has lower permeability than one Darcy, often far lower. Therefore, it has become commonplace to use smaller units such as the following:

milliDarcy ($10^{-3}$ Darcy) typical of conventional reservoirs;
microDarcy ($10^{-6}$ Darcy) typical of tight gas reservoirs; and
nanoDarcy ($10^{-9}$ Darcy) typical of shale formations.

As mentioned above, shale has exceptionally low permeability, to the extent that it was often considered impermeable by engineers and geologists studying conventional oil and gas reservoirs. When cores are taken for analysis from wells in shale formations, conventional analysis methods may not provide reliable data because the instruments and laboratory techniques were intended for use on rock with much higher permeability values. In addition, calibration standards for laboratory equipment that measures permeability, such as check plugs (permeability calibration standards that are similar in shape to core plugs), are only available for the much higher permeabilities found in conventional oil and gas reservoirs.

Laboratory instruments used to measure permeability are known as permeameters. Many types of permeameters are used in the industry. Most are designed to make measurements on core plugs, which are circular cylinders of rock, typically 1 to 1½ inches in diameter and 1 to 2 inches in length.

Permeameters may be calibrated or checked for accuracy using calibration standards, such as check plugs of known permeability values. In commercial laboratories, check plugs are commonly tested along with actual core samples from a reservoir. For example, one sample out of ten samples tested may be a check plug.

Check plugs may be sensitive to environmental factors such as humidity and mechanical stress. Furthermore, check plugs suffer from the need to empirically measure the permeability of check plugs.

The need still exists for new approaches to calibration of permeameters using check plugs. In particular, there is a need for new approaches due to a lack of available check plugs in the 10-10,000 nanoDarcy range typical of shales or mudstones.

SUMMARY OF INVENTION

One or more embodiments of the present invention provide a calibration standard or check plug in the permeability range of 10-10,000 nanoDarcy. The check plug may have similar exterior dimensions to a core sample that would be used with existing permeameters. For example, the check plug may have a diameter within the range of 0.5 to 5 inches, or within the range of 1 to 3 inches. Furthermore, one or more embodiments of a check plug may have a length within the range of 0.5 to 5 inches, or within the range of 1 to 2 inches.

One or more embodiments of the present invention provide a check plug which can be constructed from an impermeable material that is insensitive to moisture, such as metal, glass or a polymer. In addition, the check plug may be constructed from an impermeable material such that the permeability of the check plug does not change upon being exposed to a mechanical stress.

One or more embodiments of the present invention provide a check plug which has one or more cylindrical channels of a known diameter from which the permeability of the check plug may be calculated. The channel may be formed by drilling a hole in the check plug and cementing a capillary tube in the channel. The capillary tube provides an internal diameter that is measured in microns, such as less than 50 microns or between 500 nanometers and 30 microns. The annulus between the capillary tube and the hole in the check plug is sealed. The permeability of the check plug may be calculated using the well-known Hagen-Poiseuille equation, the physical law that gives the pressure drop in a fluid flowing through a long cylindrical pipe in terms of the flow rate, fluid viscosity, and geometry.

Methods for use thereof and methods of manufacture thereof are also disclosed.

BRIEF DESCRIPTION OF THE DRAWINGS

The foregoing and other advantages of the present techniques may become apparent upon reviewing the following detailed description and drawings of non-limiting examples of embodiments in which.

DETAILED DESCRIPTION

Figure 1:
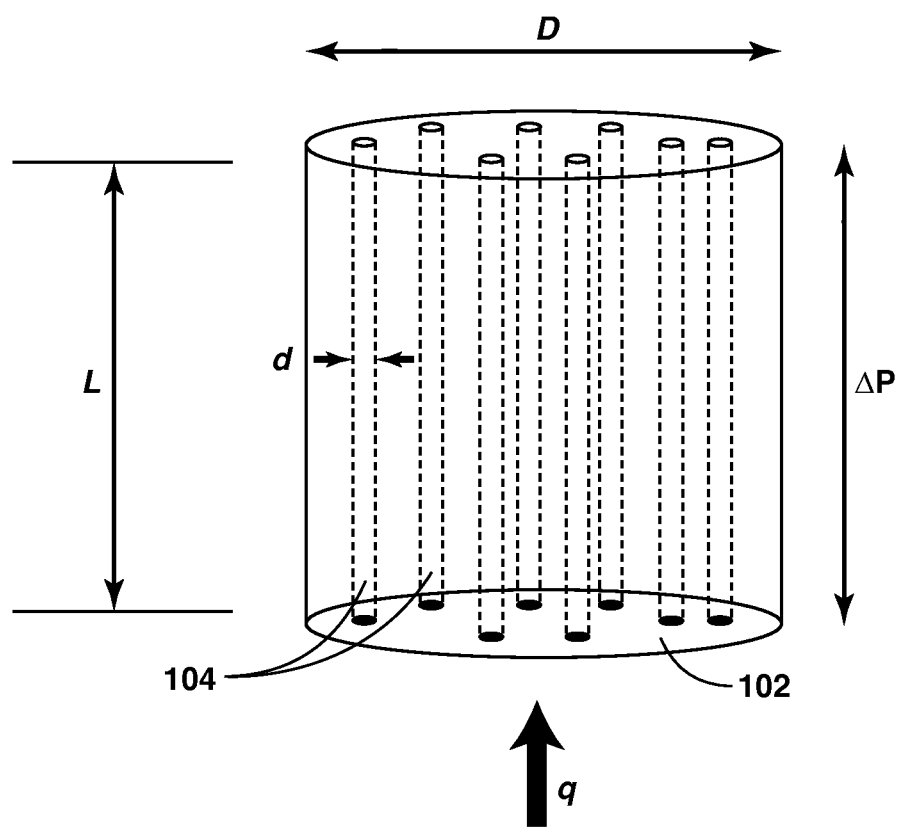
FIG. 1 is an exemplary illustration of a check plug according to an embodiment of the present invention.

In the following detailed description section, the specific embodiments of the present techniques are described in connection with preferred embodiments. However, to the extent that the following description is specific to a particular embodiment or a particular use of the present techniques, this is intended to be for exemplary purposes only and simply provides a description of the exemplary embodiments. Accordingly, the invention is not limited to the specific embodiments described below, but rather, it includes all alternatives, modifications, and equivalents falling within the true spirit and scope of the appended claims.

Embodiments herein relate to benchmarking check plug based permeability measurements for low permeability rocks. For example, the permeability values measured by different laboratories on similar shale samples have been found to vary by orders of magnitude. (See, Passey, Q. R., Bohacs, K. M., Esch, W. L., Klimentidis, R., and Sinha, S., "From Oil-Prone Source Rock to Gas-Producing Shale Reservoir—geologic and Petrophysical Characterization of Unconventional Shale-Gas Reservoirs." SPE 131350, presented at the CPS/SPE International Oil & Gas Conference and Exhibition in China, held in Beijing, China, 2010; Spears, R. W., Dudus. D., Foulds, A., Passey, Q., Sinha, S., and Esch, W. L., Shale Gas Core Analysis: Strategies for Normalizing Between Laboratories and a Clear Need for Standard Materials, SPWLA 52nd Annual Logging Symposium held in Colorado Springs, Colo., May 14-18, 2011; Paper A). The wide variance in the measured permeability values provides a high degree of uncertainty when trying to make business decisions regarding producing hydrocarbons.

Embodiments herein relate to calibration standards using permeability values for check plugs that can be calculated from first principles using the Hagen-Poiseuille equation. Calibration standards or check plugs used in the past have used porous materials for the check plugs such as natural sandstone, sintered metal, or porous ceramics. In addition to being more permeable than shale, check plugs made from these materials have the disadvantage that their permeability values are not known from calculations or first principles, but must be measured empirically. As a result, calibration of a permeameter consists of comparing the test results between two or more instruments using the same check plug. When the instruments give conflicting results, it may not be clear which measurement is correct and which is erroneous. The calibration standards described herein avoid this problem by using check plugs with permeability values that can be calculated from first principles using the Hagen-Poiseuille equation.

Embodiments herein relate to calibration standards using a check plug having minimal stress sensitivity. The permeabilities of many porous materials are known to be sensitive to the mechanical stress that is applied. This sensitivity includes not only the magnitude of the stress, but also the stress history and stress anisotropy—three-dimensional variation. The check plug with ultra-low permeability calibration standards described herein are expected to have minimal stress sensitivity, and therefore stable permeabilities.

Embodiments herein relate to calibration standards using a check plug that is nearly moisture insensitive and fairly insusceptible to mechanical damage. Actual shale samples are not suitable as calibration standards because changes in ambient humidity can change the moisture content of the shale and cause mechanical damage such as fracturing or delamination. Coring or plug cutting operations to obtain core samples with desired permeability could also introduce fractures in the samples and extensive quality control would be needed to ensure that such samples are free from induced features. The calibration standards or check plugs described herein are preferably fabricated from moisture-insensitive materials such as metal, glass, polymer and epoxy. As a result their permeability values are expected to be nearly insensitive to ambient humidity. Moreover, such samples are susceptible to minimal mechanical damage or disruption.

Embodiments herein relate to calibration standards using a check plug that has minimal sample to sample variations in permeability. The permeability values of natural or man-made porous materials can vary with subtle changes in the shape and size of their pores. As a result, samples that are intended to be identical may actually have unexpected and uncontrolled differences in properties. For the calibration standards described herein, the permeabilities depend only on properties that can be controlled and measured, such as the capillary diameter, number of capillaries, and outside diameter of the sample. As a result, sample-to-sample variations in permeability are expected to be minimal. As discussed later, this has been confirmed by fabrication and testing of samples that are intended to be identical.

Embodiments herein relate to calibration standards using a check plug that is of the same size and diameter as typical core samples and is thus able to be used on existing permeameters without hardware modifications. The check plug has a known flow resistance to gas in the range of 10-10,000 nanoDarcy. Further, flow resistance is known from first principles.

The present invention is a method to create calibration standards of known permeability by creating micron or sub-micron sized channels in an impermeable matrix of the same size as a typical core sample by embedding one or more capillary tubes of known internal in diameter in the matrix or drilling or otherwise forming controlled-sized holes in the matrix. The permeability is calculated from first principles, using the Hagen-Poiseuille equation for laminar flow in a circular conduit. It can also be verified by experimental measurements. Materials are used which are not susceptible to change from external influences such as mechanical stress, humidity, etc. The internal diameter of the channels or capillaries may be known, determined from manufacturers' specifications or by measurement using optical, micro-imaging, flow based, or other techniques. Creating the channels or capillaries to the required specifications may require micro-fabrication methods, such as photolithography, used in the electronics and/or nanotechnology industries.

Referring to FIG. 1, illustrated is an embodiment of a check plug 102 according to the present invention. The check plug 102 is a circular cylinder, with one or more capillary tubes 104, or channels, with the capillary tube 104 having a diameter d. The check plug 102 has a diameter D and a length L. In an exemplary embodiment, the diameter D of the check plug 102 is similar to that of a core plug, typically 1 or 1½ inches. A gas flow rate q is shown one end of the check plug 102 with a pressure drop ΔP across the ends of the check plug.

Using the Hagen-Poiseulle equation, the volumetric gas flow rate across a check plug, q, is given by $$q = \frac{\pi \Delta P R^4}{8\mu L}\left(\frac{P_{mean}}{P_{out}}\right), \quad \text{(eq. 1)}$$

where μ is the dynamic viscosity of the fluid, R is the inner radius of the capillary tube embedded in the plug, L is the length of the plug, $P_{mean}$ is the average of the pressures at the inlet and outlet of the plug, $P_{out}$ is the pressure at the outlet of the plug, and $\Delta P$ is the pressure drop across the ends of the plug.

Considering the channel as a porous medium, which can be characterized by Darcy's law:

$$k_{channel} = \frac{q\mu L}{\frac{\pi}{4}d^2\Delta P}\left(\frac{P_{out}}{P_{mean}}\right)$$

Equation 1 can be combined with Darcy's law in order to express the permeability of the channel as:

$$k_{channel} = \frac{d^2}{32}$$

If the diameter of the channels is very small compared to the diameter of the overall sample then the effective permeability of the check plug is given by:

$$k_{effective} \approx k_{matrix} + k_{channel}\frac{nd^2}{D^2}$$

where d is the diameter of the channels, n is the number of channels, D is the diameter of the check plug and $k_{channel}$ is the permeability of an individual channel. Since $$k_{channel} = \frac{d^2}{32}$$

then it can be shown that the effective permeability of the cylinder when the matrix is impermeable, is given by the equation $$k_{effective} = \frac{nd^4}{32D^2}. \quad (eq.\ 2)$$

The effective permeability of the check plug can thus be controlled and predicted by designing the size and number of the channels.

To achieve permeabilities similar to that of shale in shale gas formations, the inside diameter of the capillary or capillaries, d, is typically in the range of 0.005 to 0.05 millimeter (5-50 micron).

In its intended use, the check plug is placed in a permeameter and gas is made to flow through the capillaries in the same manner as it flows through a porous core plug during a permeability measurement. The volumetric gas flow rate, q, and the pressure drop, $\Delta P$, are measured in the same manner as during a permeability measurement on a core plug. The permeability of the check plug or calibration standard is calculated from Darcy's Law for a compressible fluid.

$$k = \frac{q\mu L P_{atm}}{A\Delta P P_{mean}}. \quad (eq.\ 3)$$

If equations 2 and 3 indicate the same permeability, within the stated accuracy of the permeameter, the permeameter is considered to be well-calibrated. Otherwise the cause of the discrepancy is investigated and the required changes are made.

Required Conditions for Validity of Hagen-Poiseuille Equation

In order for the Hagen-Poiseuille equation to adequately represent flow in a capillary tube, laminar flow must exist in the capillary tube. In laminar flow a gas moves through the capillary tubes parallel to the axis of the capillary tubes with no turbulence, eddies, or other disturbances. Laminar flow occurs when the dimensionless Reynolds number, defined as $$Re = \frac{\rho dv}{\mu}, \quad (eq.\ 4)$$

is less than 2100, where $\rho$ is the density of the fluid and v is the linear velocity of the fluid.

In addition, in order for the Hagen-Poiseuille equation to adequately represent flow in a capillary tube, the length of the capillary tube must be at least ten times the entrance length of the capillary tube. As gas enters a capillary, some distance is required for the flow pattern to stabilize (i.e., become "fully developed") and for the Hagen-Poiseuille equation to become valid. This distance is known as the entrance length and is on the order of $l_e$=0.035 d Re (eq. 5). A common assumption is that the Hagen-Poiseuille equation is sufficiently valid if the length of the capillary is at least 10 times the entrance length.

Figure 2:
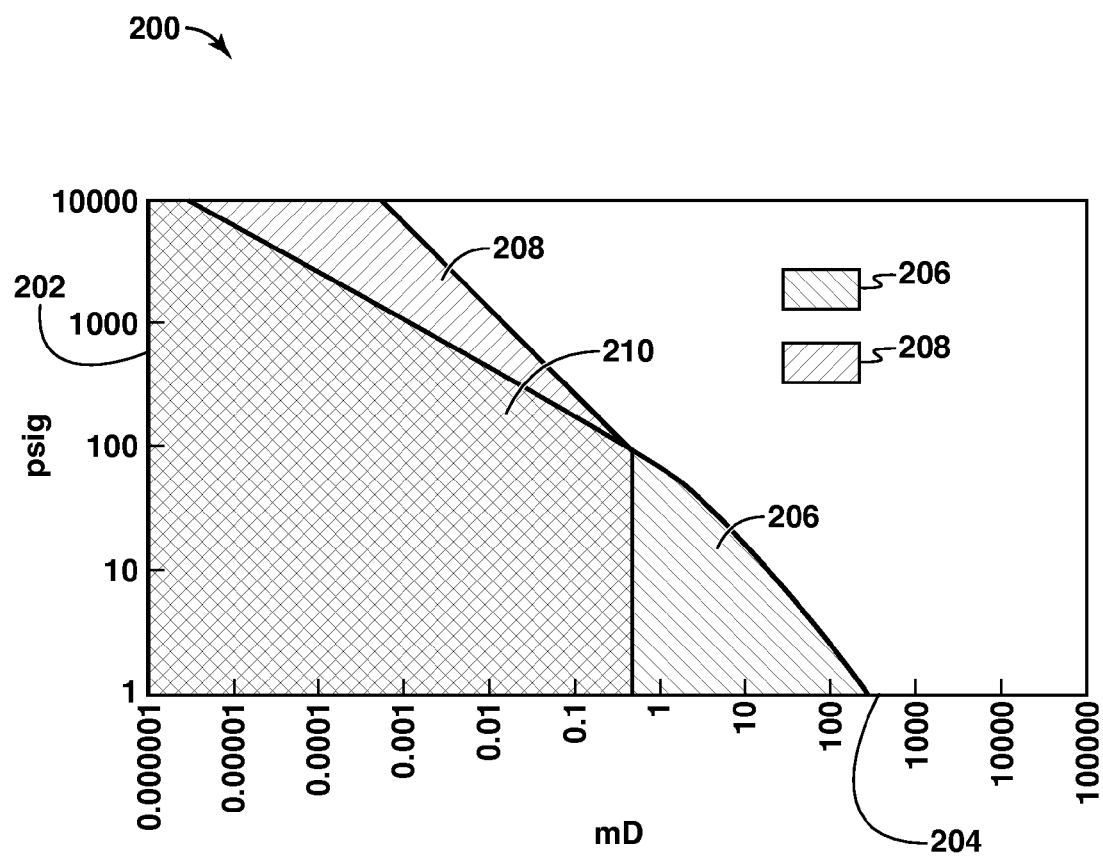
FIG. 2 is a graph of the permeability and pressure conditions that allow the Hagen-Poiseuille equation to adequately represent flow in a capillary tube.

Referring to FIG. 2, chart 200 illustrates the permeability and pressure conditions under which (a) laminar flow exists and (b) the length of the capillary is at least 10 times the entrance length for the example listed below in Table 1. The y-axis 202 lists the pressure in psig and the x-axis 204 lists the permeability in milliDarcy. Full flow region 206 is for conditions in which the downstream end of the calibration standard is open to the atmosphere. Restricted flow region 208 is for conditions in which a higher pressure is used downstream of the sample in order to maintain a specified pressure drop of 100 psi in this example. Both full flow and restricted flow are common methods used in permeability measurements; each has advantages and disadvantages depending on the permeability of the core and the pressure rating of the equipment. The full flow region 206 and restricted flow region 208 overlap in region 210.

TABLE 1

Assumptions used in determining shaded region in FIG. 12

| | |
|---|---|
| Gas | nitrogen |
| Length of calibration standard | 2 inches |
| Diameter of calibration standard | 1½ inches |
| Number of capillaries | 1 |
| Downstream pressure | atmospheric (for full flow) |
| | 100 psi below inlet pressure |
| | (for restricted flow) |

For permeability and pressure conditions not in the shaded regions of FIG. 2, the criteria for the Hagen-Poiseuille equation may still be met, depending on details such as gas composition and number of capillary holes in the calibration standard.

One of the criteria for convective flow, where the Hagen-Poiseuille equation is valid, is that the molecular mean free path of the fluid should be smaller than the physical length scale of the channel through which the fluid flows. If such a criterion is met then the fluid is said to behave as a continuum. The continuum assumption can be characterized by a Knudsen number (Kn), which is the ratio of the mean free path of the fluid to the characteristic length of the channel. If Kn<1, then the continuum assumption is valid. When Kn>>1, then the fluid is in the transition or free molecular flow range and the transport mechanism may be diffusion or a combination of convection and diffusion. The smaller the characteristic length scale of the channel, the larger would be the Knudsen number. Check plugs have been made with channels with internal diameter as small as 5 microns. The mean free path for helium gas at room conditions is 173.6 nanometers [reference 13]. The Knudsen number for helium gas while flowing through a 5 micron channel would be:

$$Kn = \frac{173.6 \times 10^{-3}}{5} = 0.035 << 1$$

As shown above, the continuum assumption is valid for all the channels that we have used in our standards. Further calculations have shown that the assumption is also valid for all pressures and permeability values shown in FIG. 2.

EXAMPLE

Six check plugs were constructed by drilling a hole along the length of a stainless steel cylinder and using epoxy to cement a precision-bore glass capillary in the hole. Glass capillaries were used with internal diameters of 5, 10, 26 and 47 microns. Three check plugs were made using a 10 micron glass capillary, the other three check plugs were made using one of the 5, 26, or 47 micron glass capillaries. The check plugs were 1 inch in length and 1.5 inches in diameter in order to fit within the permeameter. Compressed air was used to confirm that flow occurred only through the bore of the capillary, with no bypassing through the epoxy-filled annulus. Testing confirmed that the permeabilities of the check plugs or calibration standards agreed well with the permeabilities calculated from the Hagen-Poiseulle equation.

Figure 3:
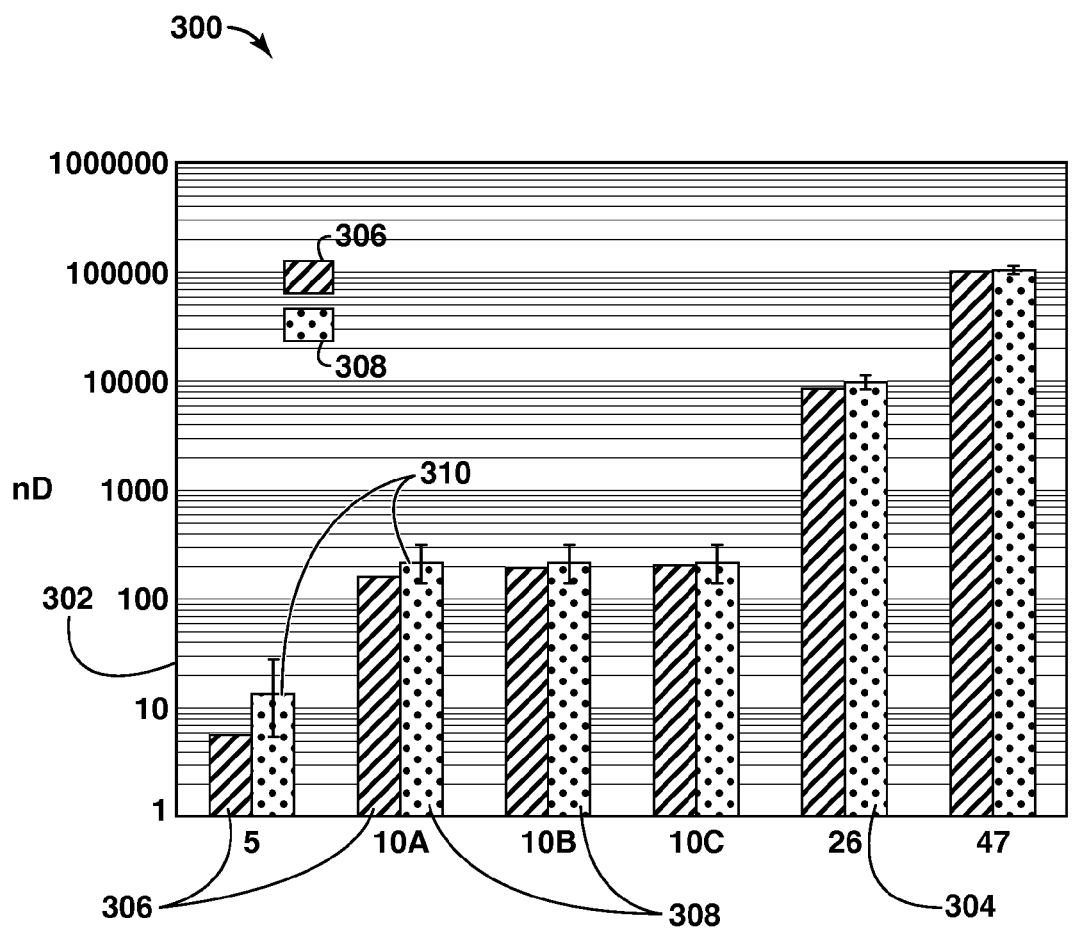
FIG. 3 is a graph of measured and calculated permeability for six check plugs constructed according to an embodiment of the present invention.

Referring to FIG. 3, illustrated is graph 300 showing the agreement between the measured and the calculated permeabilities of the six check plugs. The y-axis 302 of the graph 300 indicates the permeability in nanoDarcy on a logarithmic scale. The x-axis 304 of the graph 300 shows the six check plugs, labeled 5, 10A, 10B, 10C, 26 and 47. Check plug 5 has a 5 micron glass capillary, check plugs 10A-C each have a 10 micron glass capillary, check plug 26 has a 26 micron glass capillary, and check plug 47 has a 47 micron glass capillary. Bars 306 on the graph 300 indicate the measured permeability from a permeameter for each of the six check plugs. Bars 308 on the graph 300 indicate the calculated permeability using equation 2 for each of the six check plugs. The error bars 310 on the calculated permeability bars 308 were computed by accounting for the tolerance in the inside diameter of the capillaries, ±1 micron, that was measured by observing under a microscope, several short segments of exemplary glass capillary tubes, cut along the length of the capillaries. The larger discrepancy noted for check plug 5 is still within specifications, given the large relative tolerance for the inside diameter (5±1 micron, or ±20%) and the fourth-power dependence of permeability on diameter shown in equation 2. The close agreement between the calculated and measured permeabilities of most samples indicates that (a) the samples behaved as expected, and (b) the diameters of the capillary bores were within specifications.

While the present techniques of the invention may be susceptible to various modifications and alternative forms, the exemplary embodiments discussed above have been shown by way of example. However, it should again be understood that the invention is not intended to be limited to the particular embodiments disclosed herein. Indeed, the present techniques of the invention are to cover all modifications, equivalents, and alternatives falling within the spirit and scope of the invention as defined by the following appended claims.

What is claimed is:

1. A method of creating a check plug of known permeability comprising:
   creating a cylinder with a diameter D with an impermeable matrix;
   creating a channel in the cylinder by:
      forming a passage in the cylinder;
      attaching a glass capillary tube containing the channel within the passage; and
      sealing the annulus between the passage and the glass capillary tube,
   wherein the channel has a known diameter d of less than 50 microns; and
   calculating the permeability through the check plug by the equation $$k_{effective} = \frac{nd^4}{32D^2},$$

wherein n is the number of channels.

2. The method of claim 1 wherein the diameter d of the channel is within the range of 5-30 microns.

3. The method of claim 2 wherein the creating the channel in the cylinder further comprises micro fabrication techniques.

4. The method of claim 1 wherein the diameter D of the cylinder is within a range of 0.5 to 4 inches.

5. The method of claim 1 wherein the cylinder has a length within a range of 0.5 to 5 inches.

6. The method of claim 1 wherein the impermeable matrix is a metal.

7. The method of claim 1 wherein the impermeable matrix is a polymer.

8. The method of claim 1 wherein the impermeable matrix is a material that is insensitive to humidity.

9. The method of claim 1 wherein the impermeable matrix is a material whose permeability has minimal sensitivity to mechanical stress.

10. The method of claim 1 wherein the calculated permeability is in a range of 10-10,000 nanoDarcy.

11. A check plug of known permeability comprising:
    a cylinder with a diameter D,
    wherein the cylinder comprises an impermeable matrix;
    one or more glass capillary tubes is sealed in the cylinder to form channels,
    wherein the channel has a known diameter d; and
    the permeability through the check plug can be calculated by the equation $$k_{effective} = \frac{nd^4}{32D^2},$$

wherein n is the number of channels.

12. The check plug of claim 11 wherein the diameter d of the one or more channels is less than 50 microns.

13. The check plug of claim 11 wherein the diameter d of the one or more channels is within the range of 5-30 microns.

14. The check plug of claim 13 wherein the channels are created by:
   forming a passage in the cylinder;
   attaching the glass capillary tube containing the channel within the passage, and
   sealing the annulus between the passage and the glass capillary tube.

15. The check plug of claim 13 wherein the channels are created by micro fabrication techniques.

16. The check plug of claim 11 wherein the diameter D of the cylinder is within a range of 0.5 to 4 inches.

17. The check plug of claim 11 wherein the cylinder has a length within a range of 0.5 to 5 inches.

18. The check plug of claim 11 wherein the impermeable matrix is a metal.

19. The check plug of claim 11 wherein the impermeable matrix is a polymer.

20. The check plug of claim 11 wherein the permeability does not change in response to humidity.

21. The check plug of claim 11 wherein the permeability has minimal sensitivity to mechanical stress.

22. The check plug of claim 11 wherein the calculated permeability is in a range of 10-10,000 nanoDarcy.

\* \* \* \* \*